US009149366B2

(12) United States Patent
Prevost et al.

(10) Patent No.: US 9,149,366 B2
(45) Date of Patent: Oct. 6, 2015

(54) ADAPTABLE INTERBODY IMPLANT AND METHODS OF USE

(71) Applicant: Warsaw Orthopedic, Inc., Warsaw, IN (US)

(72) Inventors: Julien J. Prevost, Memphis, TN (US); Thomas A. Carls, Memphis, TN (US); Russell P. Nockels, River Forest, IL (US)

(73) Assignee: Warsaw Orthopedic, Inc., Warsaw (IN)

( * ) Notice: Subject to any disclaimer, the term of this patent is extended or adjusted under 35 U.S.C. 154(b) by 127 days.

(21) Appl. No.: 13/826,825

(22) Filed: Mar. 14, 2013

(65) Prior Publication Data

US 2014/0277484 A1    Sep. 18, 2014

(51) Int. Cl.
*A61F 2/44* (2006.01)
*A61F 2/30* (2006.01)

(52) U.S. Cl.
CPC ............... *A61F 2/4455* (2013.01); *A61F 2/447* (2013.01); *A61F 2002/30563* (2013.01); *A61F 2002/30777* (2013.01); *A61F 2002/30779* (2013.01); *A61F 2002/30785* (2013.01); *A61F 2002/30904* (2013.01); *A61F 2002/4475* (2013.01); *A61F 2310/00017* (2013.01); *A61F 2310/00023* (2013.01); *A61F 2310/00029* (2013.01); *A61F 2310/00179* (2013.01)

(58) Field of Classification Search
CPC ......... A61F 2/44; A61F 2/442; A61F 2/4425; A61F 2002/443; A61F 2/4455; A61F 2002/4475

USPC ............................................ 623/17.11–17.16
See application file for complete search history.

(56) References Cited

U.S. PATENT DOCUMENTS

| 7,578,849 B2 * | 8/2009 | Trieu .......................... 623/17.15 |
| 8,083,796 B1 * | 12/2011 | Raiszadeh et al. ......... 623/17.11 |
| 2002/0077702 A1 * | 6/2002 | Castro ......................... 623/17.16 |
| 2004/0127994 A1 * | 7/2004 | Kast et al. .................. 623/17.16 |
| 2005/0125063 A1 * | 6/2005 | Matge et al. ............... 623/17.13 |
| 2008/0161920 A1 | 7/2008 | Melkent |
| 2009/0112326 A1 * | 4/2009 | Lehuec et al. ............. 623/17.16 |
| 2010/0234956 A1 * | 9/2010 | Attia et al. ................. 623/17.16 |
| 2011/0029087 A1 | 2/2011 | Haider et al. |
| 2011/0093075 A1 * | 4/2011 | Duplessis et al. .......... 623/17.16 |

* cited by examiner

*Primary Examiner* — Eduardo C Robert
*Assistant Examiner* — Julianna N Harvey

(57) ABSTRACT

An intervertebral fusion implant comprises a body defining a longitudinal axis and extending between a first end and a second end. The body defines a first wall configured for engaging a first vertebral surface and a second wall configured for engaging a second vertebral surface. The first wall is connected to the second wall. The first wall is movable relative to the second wall such that the body is deformable from a first, initial implanted configuration such that the body is disposed between the first vertebral surface and the second vertebral surface for fixation thereof and a second configuration such that the body is deformed relative to the first configuration to adapt to an orientation of the first vertebral surface and the second vertebral surface. Methods of use are disclosed.

20 Claims, 13 Drawing Sheets

ADAPTABLE INTERBODY IMPLANT AND METHODS OF USE

TECHNICAL FIELD

The present disclosure generally relates to medical devices, systems and methods for the treatment of musculoskeletal disorders, and more particularly to an adaptable interbody implant system and method for treating a vertebral column.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. These treatments may employ interbody implants. This disclosure describes an improvement over these prior art technologies.

SUMMARY

Accordingly, an adaptable interbody implant system and method are disclosed. In one embodiment, an intervertebral fusion implant is provided. The intervertebral fusion implant comprises a body defining a longitudinal axis and extending between a first end and a second end. The body defines a first wall configured for engaging a first vertebral surface and a second wall configured for engaging a second vertebral surface. The first wall is connected to the second wall. The first wall is movable relative to the second wall such that the body is deformable from a first, initial implanted configuration such that the body is disposed between the first vertebral surface and the second vertebral surface for fixation thereof and a second configuration such that the body is deformed relative to the first configuration to adapt to an orientation of the first vertebral surface and the second vertebral surface.

In one embodiment, the intervertebral fusion implant comprises a body defining a longitudinal axis and extending between a first end and a second end. The body defines a first wall configured for engaging a first vertebral surface and a second wall configured for engaging a second vertebral surface. The first wall is connected to the second wall such that the walls extend from the first end in a cantilevered configuration. The first wall defines an arcuate inner surface and the second wall defines an arcuate inner surface. The inner surfaces define a deformation cavity and the walls are configured to collapse in the cavity such that the body selectively deforms in a range between a spaced apart distance between the walls and engagement of the walls. The first wall is movable relative to the second wall such that the body is deformable from a first, initial implanted configuration such that the body is disposed between the first vertebral surface and the second vertebral surface for fixation thereof, and a second configuration such that the body is deformed relative to the first configuration to adapt to surface geometry and height of an intervertebral space between the first vertebral surface and the second vertebral surface.

In one embodiment, the intervertebral fusion implant comprises a body defining a longitudinal axis and extending between a first end and a second end. The body defines a first wall configured for engaging a first vertebral surface and a second wall configured for engaging a second vertebral surface. The walls include a first pair of lateral arms and a second pair of lateral arms. Each of the pair of lateral arms extends between the first end and the second end and define a cavity therebetween. The arms are configured to collapse in the cavities during deformation. Each of the pair of arms include at least one post disposed therebetween. The post extends a first distance. The first wall is movable relative to the second wall such that the body is selectively deformable from a first, initial implanted configuration such that the walls are spaced apart a second distance. The second distance is greater than the first distance, and the body is disposed between the first vertebral surface and the second vertebral surface for fixation thereof, and a second configuration such that the body is selectively deformed according to a difference between the first distance relative to the second difference to adapt to an orientation of the first vertebral surface and the second vertebral surface.

BRIEF DESCRIPTION OF THE DRAWINGS

The present disclosure will become more readily apparent from the specific description accompanied by the following drawings, in which.

DETAILED DESCRIPTION

Figure 1:
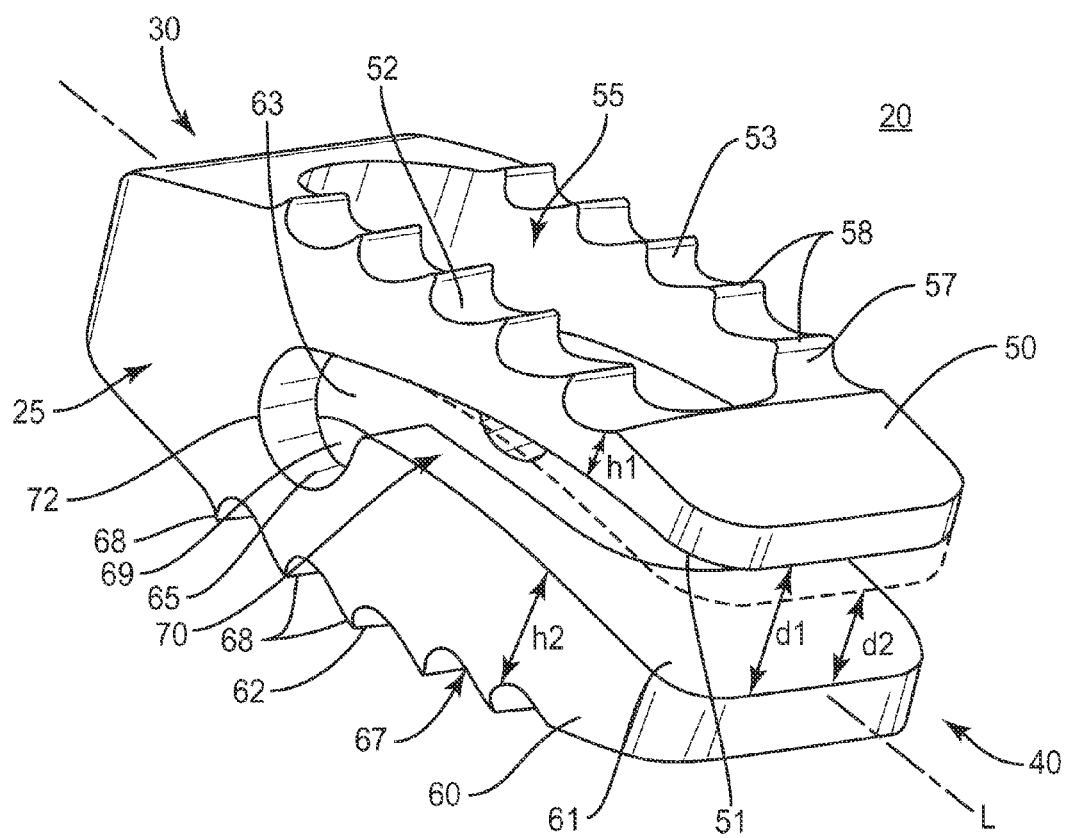
FIG. 1 is a perspective view of one particular embodiment of an implant of a system in accordance with the principles of the present disclosure.

The exemplary embodiments of an interbody implant system and related methods of use disclosed herein are discussed in terms of medical devices for the treatment of musculoskeletal disorders and more particularly, in terms of an adaptable interbody implant system and related methods for treating a vertebral column. It is envisioned that the implant system may include a self-adapting interbody implant that can deform to contact endplate surfaces of vertebrae and reduce subsidence and expulsion of the implant from an intervertebral disc space.

In one embodiment, the interbody implant deforms due to axial loading and allows increased contact with the endplate surface(s). It is contemplated that the implant has a viscoelasticity to self-adjust, for example, a deformed configuration, based on the weight of a patient. It is further contemplated that the implant is configured to have an adjustability, flexibility, deformability, strength and/or rigidity to avoid subsidence at an instrumented level or expulsion from an intervertebral space. In one embodiment, the implant has such a configuration and can resist an axial load, applied to a disc in a standing position, with 20 degree flexion and with 20 kilogram weights in a patient's hands, approximately equal to 2300 Newtons.

For example, during an interbody fusion surgery, such as, for example, an anterior lumbar interbody fusion (ALIF), direct lateral interbody fusion (DLIF) or transforaminal lumbar interbody fusion (TLIF), a surgeon prepares endplates of vertebrae prior to inserting an implant. In some applications, the endplates may not conform to the geometry of the implant. In one embodiment, the present adaptable interbody implant is configured to limit the amount of deformation allowable for the superelastic metallic alloys to affect behavior of the adaptable interbody implant, such as, for example, viscoelasticity. This configuration of the adaptable interbody implant facilitates surface contact with the endplates.

In one embodiment, the interbody implant system is configured such that an adaptable interbody implant can settle and conform to uneven and/or curved vertebral endplates before settling into a rigid, unmoving position relative to the endplates. It is envisioned that this configuration allows fusion to occur between the endplates. In one embodiment, the adaptable interbody implant includes cut-outs that may be interspersed with posts to maintain a minimum height of the implant after settling/relaxation has occurred.

It is envisioned that an adaptable interbody implant and methods of use disclosed herein can be employed to obtain fusion of vertebrae through a minimally invasive or percutaneous technique. In one embodiment, an adaptable interbody implant and methods of use can provide improved spinal treatment with a device that is variably deformable in a self-adjusting configuration including for example, fully collapsible, controlled deformation, selectively deformable at sections of the implant and/or lordotically deformable. It is contemplated that the adaptable interbody implant and methods of use disclosed herein provide a cavity of relatively large volume for post-packing of at least one agent, for example, bone graft.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed adaptable interbody implant may be alternatively employed in a surgical treatment with a patient in a prone or supine position, and/or employ various surgical approaches to the spine, including anterior, posterior, postero-rior mid-line, medial, lateral, postero-lateral, and/or antero-lateral approaches, and in other body regions. The adaptable interbody implant of the present disclosure may also be alternatively employed with procedures for treating the lumbar, cervical, thoracic and pelvic regions of a spinal column. The adaptable interbody implant and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, outer, inner, terminal (denoting position or location), left and right, posterior, anterior, and the like, are for illustrative purposes only and can be varied within the scope of the disclosure. For example, the references "superior" and "inferior" are relative and used only in the context to the other, and are not necessarily "upper" and "lower".

Further, as used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (for example, preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, for example, arresting its development, or relieving the disease, for example, causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of an adaptable interbody implant and related methods of employing the adaptable interbody implant in accordance with the principles of the present disclosure. Alternate embodiments are also disclosed. Reference will now be made in detail to the exemplary embodiments of the present disclosure, which are illustrated in the accompanying figures. Turning now to FIG. 1, there is illustrated components of an interbody implant system including an intervertebral fusion implant 20 in accordance with the principles of the present disclosure.

The components of the system can be fabricated from biologically acceptable materials suitable for medical applications, including metals, synthetic polymers, ceramics and bone material and/or their composites, depending on the particular application and/or preference of a medical practitioner. For example, the components of the system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (for example, Nitinol, super elasto-plastic metals, such as GUM METAL® manufactured by Toyota Material Incorporated of Japan), ceramics and composites thereof such as calcium phosphate (for example, SKELITE™ manufactured by Biologix Inc.), thermoplastics such as polyaryl ether ketone (PAEK) including polyether ether ketone (PEEK), polyether ketone ketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polylactide, polyglycolide, polytyrosine carbonate, polycaprolactone and their combinations. Various components of the system may be fabricated from material composites, including the above materials, to achieve various desired characteristics such as strength, rigidity, elasticity, flexibility, compliance, biomechanical performance, durability and radiolucency or imaging preference. The components of the system, individually or collectively, may also be fabricated from a heterogeneous material such as a combination of two or more of the above-described materials.

The system including intervertebral fusion implant 20 can be employed as a stabilization device in fusion and fixation procedures, for example, for patients suffering from a spinal disorder to provide height restoration between vertebral bodies, decompression, restoration of lordosis and/or resistance of subsidence into vertebral endplates. The components of the system may be monolithically formed, integrally connected or include fastening elements and/or instruments, for example, as described herein.

Intervertebral fusion implant 20 includes a body 25 defining a longitudinal axis L and extending between a first end, such as, for example, an anterior end 30 and a second end, such as, for example, a posterior end 40. Body 25 includes a first wall 50 and a second wall 60. First wall 50 is configured to engage a first vertebral surface and second wall 60 is configured to engage a second vertebral surface facing in an orientation opposing the first vertebral surface. Walls 50, 60 extend in a substantially linear orientation along axis L from anterior end 30. It is envisioned that walls 50, 60 may extend in alternate configurations such as, for example, having a radius of curvature, transverse, angular, offset and/or staggered. Each of walls 50, 60 have a substantially rectangular cross section configuration. It is envisioned that walls 50, 60 may have various cross section configurations, such as, for example, oval, oblong, triangular, square, polygonal, irregular, uniform, non-uniform, variable, hollow and/or tapered.

Walls 50, 60 are flexible and relatively movable. First wall 50 and second wall 60 are connected at anterior end 30. First wall 50 and second wall 60 extend in a cantilevered configuration from anterior end 30. It is envisioned that wall 50 and/or wall 60 may be flexible, semi-rigid or rigid.

Wall 50 includes an outer wall surface 57 configured to engage a first vertebral endplate surface. Wall surface 57 includes a plurality of raised elements 58. Raised elements 58 are configured to enhance fixation and/or gripping with vertebral tissue. Wall 60 includes an outer wall surface 58 configured to engage a second vertebral endplate surface. Wall surface 67 includes a plurality of raised elements 68. Raised elements 68 are configured to enhance fixation and/or gripping with vertebral tissue. Raised elements 58, 68 are disposed transverse to longitudinal axis L. It is envisioned that all or only a portion of first and second wall surfaces 57, 67 may have raised elements or alternate surface configurations to enhance fixation with tissue such as, for example, rough, arcuate, undulating, mesh, porous, semi-porous, dimpled and/or textured according to the requirements of a particular application. It is further envisioned that elements 58, 68 may be disposed at alternate orientations, relative to axis L, such as, for example, perpendicular and/or other angular orientations such as acute or obtuse, co-axial and/or may be offset or staggered. It is envisioned that raised elements 58, 68 may be fabricated from the same or alternate material as body 25.

First wall 50 includes an inner surface 51 extending from anterior end 30. Inner surface 51 has a substantially smooth and/or even surface and is arcuately shaped in a concave configuration. Second wall 60 includes an inner surface 61 extending from anterior end 30. Inner surface 61 has a substantially smooth and/or even surface and is arcuately shaped in a convex configuration. It is envisioned that all or only a portion of inner surfaces 51, 61 may have alternate surface configurations such as, for example, rough, arcuate, undulating, mesh, porous, semi-porous, dimpled and/or textured, and/or inner surfaces 51, 61 may be engageable, according to the requirements of a particular application.

First wall 50 and second wall 60 are configured to form a cavity 70. Inner surfaces 51, 61 define cavity 70, which extends along axis L. Cavity 70 has an arcuate configuration. Wall 60 includes recesses 72, disposed on lateral portions of body 25. Each recess 72 defines an opening 65, which is in communication with cavity 70. Opening 65 is substantially circular and provides a relief to facilitate relative movement of walls 50, 60. It is envisioned that one or both of recesses 72 may have various cross section configurations, such as, for example, oval, oblong, triangular, square, polygonal, irregular, uniform, non-uniform, variable and/or tapered.

First wall 50 includes a pair of lateral spaced apart arms 52, 53 extending along axis L between anterior end 30 and posterior end 40. Lateral arms 52, 53 are spaced apart to define an opening 55. Opening 55 is in communication with cavity 70. It is envisioned that opening 55 may have various configurations, such as, for example, oval, oblong, triangular, square, polygonal, irregular, uniform, non-uniform, offset, staggered, undulating, arcuate, variable and/or tapered. It is contemplated that first wall 50 may include one or a plurality of openings.

Arms 52, 53 each have a rectangular cross section. It is contemplated that arms 52, 53, can have alternative cross section configurations, such as, for example, oval, oblong, triangular, square, polygonal, irregular, uniform, non-uniform, offset, staggered, undulating, arcuate, variable and/or tapered. Arms 52, 53 are connected to a planar portion of posterior end 40. The planar portion has a uniform thickness.

Second wall 60 includes a pair of lateral spaced apart arms 62, 63 adjacent anterior end 30. Arms 62, 63 are spaced apart to define an opening 69 adjacent anterior end 30. Opening 69 is in communication with cavity 70. It is envisioned that cavity 70, opening 55, opening 65 and/or opening 69 may be configured for packing of at least one agent, for example, bone graft. It is further envisioned that opening 65 may have alternate configurations, such as, for example, oval, oblong, triangular, square, polygonal, irregular, uniform, non-uniform, offset, staggered, undulating, arcuate, variable and/or tapered. It is contemplated that first wall 50 may include one or a plurality of openings.

In operation, intervertebral fusion implant 20 is disposable in a first, initial implanted configuration (FIG. 2) such that body 25 is disposed between a first vertebral surface and a second vertebral surface for fixation of intervertebral fusion implant 20 with vertebrae. Wall 50 is movable relative to wall 60 such that body 25 is deformable from the first configuration to a second configuration (FIG. 3) such that body 25 is deformed relative to the first configuration to adapt to an orientation of the first vertebral surface and the second vertebral surface. It is contemplated that the orientation of the vertebral surface can include surface geometry, distraction height and/or relative angular orientation.

Inner surfaces 51, 61 define cavity 70 such that cavity 70 is configured as a deformation cavity. Walls 50, 60 are configured to collapse in cavity 70 such that body 25 selectively deforms in a range between a spaced apart distance d1 between walls 50, 60 and a relative distance d2 between walls 50, 60. It is envisioned that distance d2 can include a range of distance including distance d1, a distance less than distance d1 and distance substantially equal to zero such that walls 50, 60 are disposed in a flush engagement.

The second configuration includes body 25 being deformed relative to the first configuration in an orientation such that intervertebral fusion implant 20 adapts to a surface geometry and a height of an intervertebral space between the first vertebral surface and the second vertebral surface. This configuration of intervertebral fusion implant 20 facilitates surface contact with vertebral endplates. In one embodiment, intervertebral fusion implant 20 is configured to settle over a duration of time and conform to uneven and/or curved vertebral endplates before settling into a rigid, unmoving position relative to the endplates. It is envisioned that this configuration allows fusion to occur between the endplates. In one embodiment, intervertebral fusion implant 20 includes cutouts interspersed with posts to maintain a minimum height of intervertebral fusion implant 20 after settling/relaxation.

In one embodiment, walls 50, 60 are configured to collapse and deform upon pressure being applied by the vertebrae. It is envisioned that such collapse includes collapse of wall 50 including arms 53, 63. For example, upon implantation of intervertebral fusion implant 20 between a first vertebra and a second vertebra, intervertebral fusion implant 20 is disposed in the first configuration such that wall 50 is spaced apart a distance d1 from wall 60. After a duration of time, intervertebral fusion implant 20 is configured to deform to a second configuration such that wall 50 and second wall 60 collapse and are spaced apart a distance d2. In one embodiment, intervertebral fusion implant 20 is adaptable and variably deformable in a self-adjusting configuration over a natural and/or selected duration of time. Deformation can occur immediately or can take up to a week. In some cases, optimal deformation may take up to six months. Deformation time depends upon the surgical approach and/or anatomical correction desired. It is envisioned that intervertebral fusion implant 20 can be fully collapsible, have a controlled and/or selected deformation based on duration of implantation, material, and/or patient features, selectively deformable at sections of intervertebral fusion implant 20 and/or lordotically deformable.

In one embodiment, wall 60 can be fixed, semi-rigid or rigid and wall 50 is flexible. It is envisioned that wall 50 and/or wall 60 can be pivotable and/or rotatable relative to anterior end 30. In one embodiment, inner surfaces 51, 61 are configured for complimentary engagement, such that upon collapse, inner surface 51 is in flush engagement with inner surface 61. It is envisioned that the height and/or thickness of walls 50 and 60, h1 and h2, respectively, can be altered to selectively control deformation of intervertebral fusion implant 20.

Figure 2:
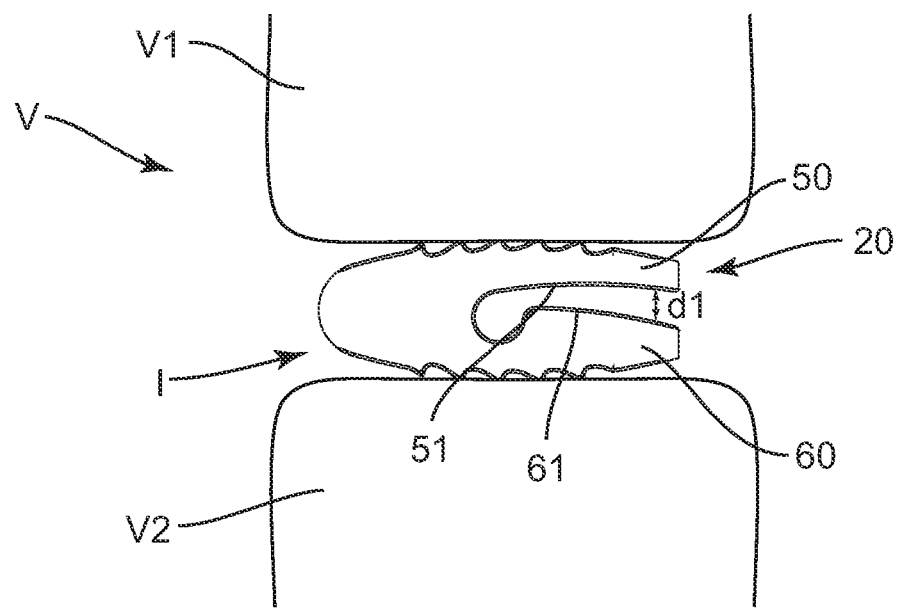
FIG. 2 is a side view of components of the system shown in FIG. 1 disposed with vertebrae.
Figure 3:
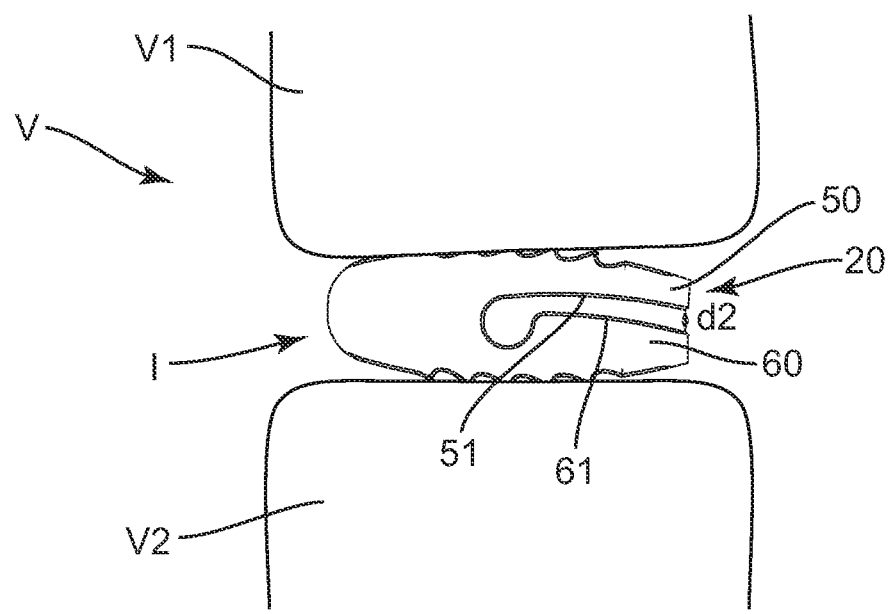
FIG. 3 is a side view of components of the system and vertebrae shown in FIG. 2.

In assembly and use, the interbody implant system including intervertebral fusion implant 20, similar to that described with regard to FIG. 1, is employed with a surgical procedure, such as, a fusion treatment of a spine of a patient including vertebrae V, intervertebral disc space I and body areas adjacent thereto, as shown in FIGS. 2 and 3. The interbody implant system may also be employed with other surgical procedures, such as, for example, discectomy, laminotomy, laminectomy, nerve root retraction, foramenotomy, facetectomy, decompression, and spinal, nucleus or disc replacement.

For example, the interbody implant system can be employed with a surgical arthrodesis procedure, such as, for example, an interbody fusion for treatment of an applicable condition or injury of an affected section of a spinal column and adjacent areas within a body, such as, for example, intervertebral disc space I between first vertebrae V1 and second vertebrae V2 of vertebrae V. It is contemplated that intervertebral fusion implant 20 of the interbody implant system, described above, can be inserted with intervertebral disc space I to space apart articular joint surfaces, provide support and maximize stabilization of vertebrae V. It is further contemplated that intervertebral fusion implant 20 provides height restoration between vertebral bodies, decompression, restoration of sagittal balance and/or resistance of subsidence into vertebral endplates.

In use, to treat the affected section of vertebrae V, a medical practitioner obtains access to a surgical site including vertebrae V in any appropriate manner, such as through incision and retraction of tissues. It is envisioned that the interbody implant system can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure is performed for treating the spine disorder. Intervertebral fusion implant 20, described with regard to FIG. 1, is then employed to augment the surgical treatment. Intervertebral fusion implant 20 can be delivered or implanted as a pre-assembled device or can be assembled in situ. Intervertebral fusion implant 20 can be completely or partially revised, removed or replaced in situ. It is contemplated that one or all of the components of the interbody implant system can be delivered to the surgical site via manual manipulation and/or a free hand technique. It is further contemplated that intervertebral fusion implant 20 may be inserted posteriorly, and then manipulated anteriorly and/or lateral and/or medial.

An incision is made in the body of a patient and a cutting instrument (not shown) creates a surgical pathway for implantation of intervertebral fusion implant 20 within the patient body. A guide instrument (not shown) is employed to initially distract vertebrae V1 from vertebrae V2. A sleeve or cannula (not shown) is used to access intervertebral disc space I and facilitate delivery and access for components of the interbody implant system. A preparation instrument (not shown) can be inserted within the sleeve or cannula and disposed within intervertebral disc space I. The preparation instrument(s) can be employed to remove some or all of the disc tissue including the disc nucleus and fluids, adjacent tissues and/or bone, corticate, scrape and/or remove tissue from the surfaces of endplates of opposing vertebrae V1, V2, as well as for aspiration and irrigation of the region according to the requirements of a particular surgical application.

Intervertebral fusion implant 20 is delivered through a surgical pathway along a substantially postero-lateral approach into intervertebral disc space I with a delivery instrument (not shown) including a driver. The driver delivers intervertebral fusion implant 20 into the prepared intervertebral disc space I, between vertebrae V1 and vertebrae V2, according to the requirements of a particular surgical application. It is contemplated that intervertebral fusion implant 20 is delivered through a surgical pathway along a substantially lateral approach to correct coronal deformities.

Upon desired positioning of intervertebral fusion implant 20, implant 20 is disposed in a first, initial implanted configuration (FIG. 2) such that body 25 is disposed between and engaging a surface of vertebra V1 and a surface of vertebra V2 for fixation of intervertebral fusion implant 20 with vertebrae V. Inner surface 51 of wall 50 is spaced apart a distance d1 from inner surface 61 of wall 60. Wall 50 is movable relative to wall 60 such that body 25 is deformable from the first configuration to a second configuration (FIG. 3) such that body 25 is deformed relative to the first configuration to adapt to an orientation of the surface of vertebra V1 and a surface of vertebra V2. After a duration of time, as discussed above, intervertebral fusion implant 20 is configured to deform, due to duration of implantation, material, surgical manipulation and/or patient features such as for example settling to conform to uneven and/or curved surfaces of the endplates, to the second configuration such that wall 50 and second wall 60 collapse and are spaced apart a distance d2. Walls 50, 60 collapse in cavity 70 such that body 25 selectively deforms in a range between a spaced apart distance d1 between walls 50, 60 and a relative distance d2 between walls 50, 60.

The second configuration includes body 25 being deformed relative to the first configuration in an orientation such that intervertebral fusion implant 20 adapts to a surface geometry and a height of an intervertebral space between the surfaces of vertebrae V1, V2. This configuration of intervertebral fusion implant 20 facilitates surface contact with vertebral endplates before settling into a rigid, unmoving position relative to the endplates of vertebrae V1, V2.

It is envisioned that the components of the interbody implant system, which may include one or a plurality of intervertebral fusion implants 20, can be delivered to the surgical site via alternate approaches. In one embodiment, intervertebral fusion implant 20 is delivered through the surgical pathway along a transforaminal lumbar interbody fusion approach into intervertebral disc space I and disposed in the expanded configuration. In one embodiment, a plurality of intervertebral fusion implants 20 are delivered through the surgical pathway along a posterior lumbar interbody fusion approach into intervertebral disc space I and disposed in the expanded configuration in a side by side orientation.

In one embodiment, the interbody implant system includes an agent, which can include a bone growth promoting material, which may be disposed, packed or layered within, on or about the components and/or surfaces of the interbody implant system. The bone growth promoting material, such as, for example, bone graft can be a particulate material, which may include an osteoconductive material such as HA and/or an osteoinductive agent such as a bone morphogenic protein (BMP) to enhance bony fixation of intervertebral fusion implant 20 with the adjacent vertebrae.

It is contemplated that the agent and/or bone graft may include therapeutic polynucleotides or polypeptides. It is further contemplated that the agent and/or bone graft may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. Intervertebral fusion implant 20 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

Figure 4:
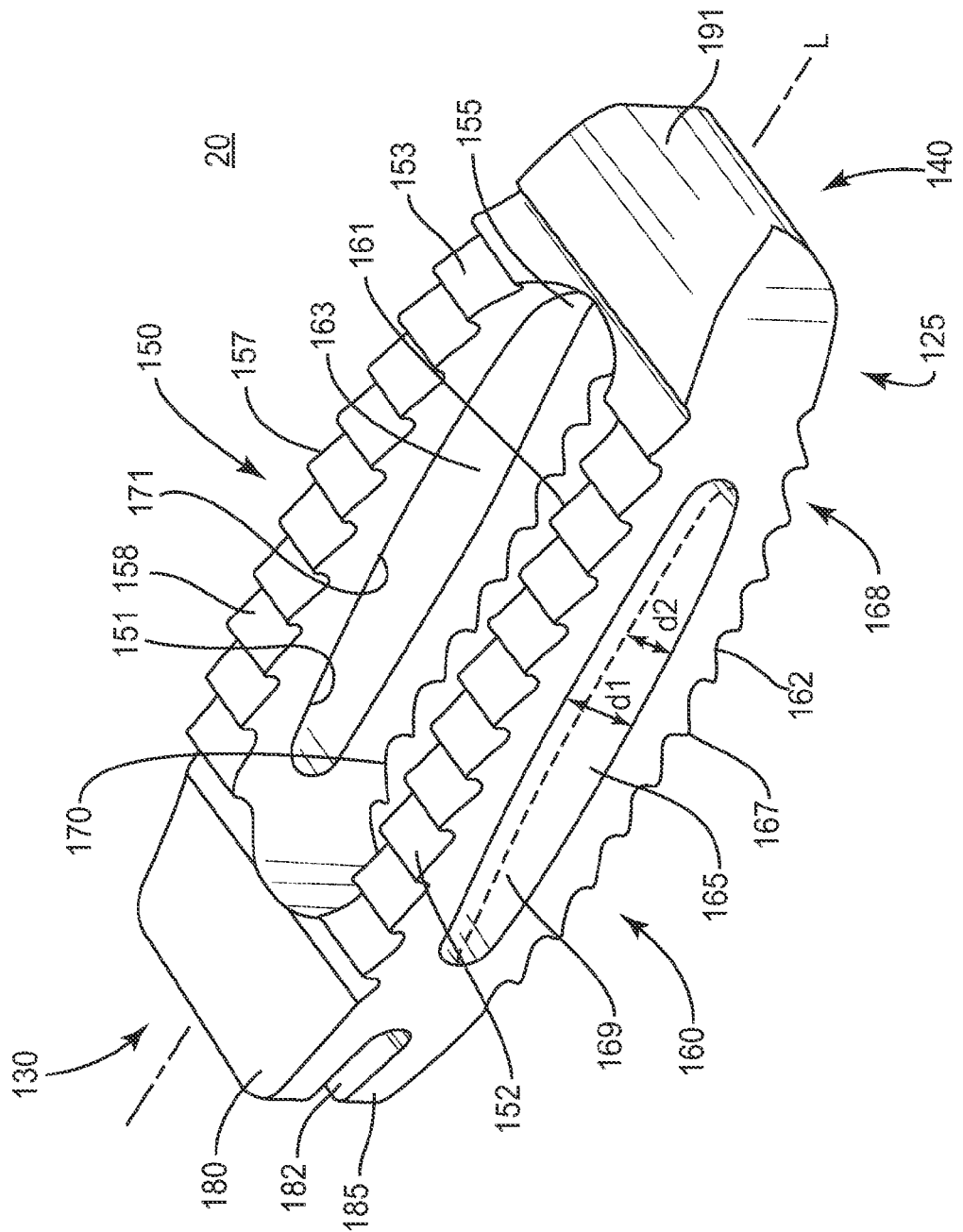
FIG. 4 is a perspective view of one embodiment of the implant shown in FIG. 1.

In one embodiment, as shown in FIG. 4, the interbody implant system includes an intervertebral fusion implant 20, similar to the configuration and methods described above with regard to FIGS. 1-3, which includes a body 125 defining a longitudinal axis L and extending between an anterior end 130 and a posterior end 140. Body 125 includes a first wall 150 and a second wall 160. First wall 150 is configured to engage a first vertebral surface and second wall 160 is configured to engage a second vertebral surface facing in an orientation opposing the first vertebral surface. Walls 150, 160 extend in a substantially linear orientation along axis L from anterior end 130.

Walls 150, 160 are flexible and relatively movable. Wall 150 includes an outer wall surface 157 configured to engage a first vertebral endplate surface. Wall surface 157 includes a plurality of raised elements 158. Wall 160 includes an outer wall surface 167 configured to engage a first vertebral endplate surface. Wall surface 167 includes a plurality of raised elements 168.

First wall 150 includes an inner surface 151 extending from anterior end 130. Inner surface 151 has a substantially smooth and/or even surface and is arcuately shaped in a concave configuration. Second wall 160 includes an inner surface 161 extending from anterior end 130. Inner surface 161 has a substantially smooth and/or even surface and is arcuately shaped in a concave configuration.

First wall 150 and second wall 160 are configured to form a cavity 170. First wall 150 includes a pair of lateral spaced apart arms 152, 153 extending along axis L between anterior end 130 and posterior end 140. Lateral arms 152, 153 are spaced apart to define an opening 155. Opening 155 is in communication with cavity 170.

Second wall 160 includes a pair of lateral spaced apart arms 162, 163 extending along axis L between anterior end 130 and posterior end 140. Lateral arms 162, 163 are spaced apart to define an opening 165. Opening 165 is in communication with cavity 170. Arms 152, 162 define a lateral opening 169 and arms 153, 163 define a lateral opening 171. Openings 169, 171 communicate with cavity 170. It is envisioned that cavity 170, opening 155, opening 165, opening 169 and/or opening 171 may be configured for packing of at least one agent, for example, bone graft.

Arms 152, 153, 162, 163 are connected to a solid nose portion 191 of posterior end 140. Nose portion 191 has tapered thickness. Arms 152, 153, 162, 163 are connected to arms 180, 185 that extend outwardly from anterior end 130. Arms 180, 185 form a cavity 182. Arms 180, 185 are configured to collapse into cavity 182 during deformation, as described below.

In operation, walls 150, 160 are configured to collapse in cavity 170 such that body 125 selectively deforms in a range between a spaced apart distance d1 between walls 150, 160 and a relative distance d2 between walls 150, 160 such that intervertebral fusion implant 20 is disposable between a first, initial implanted configuration and a second configuration, similar to that described herein, such that body 125 is deformed relative to the first configuration to adapt to an orientation of the first vertebral surface and the second vertebral surface. It is envisioned that distance d2 can include a range of distance including distance d1, a distance less than distance d1 and distance substantially equal to zero such that walls 150, 160 are disposed in a flush engagement.

Figure 5:
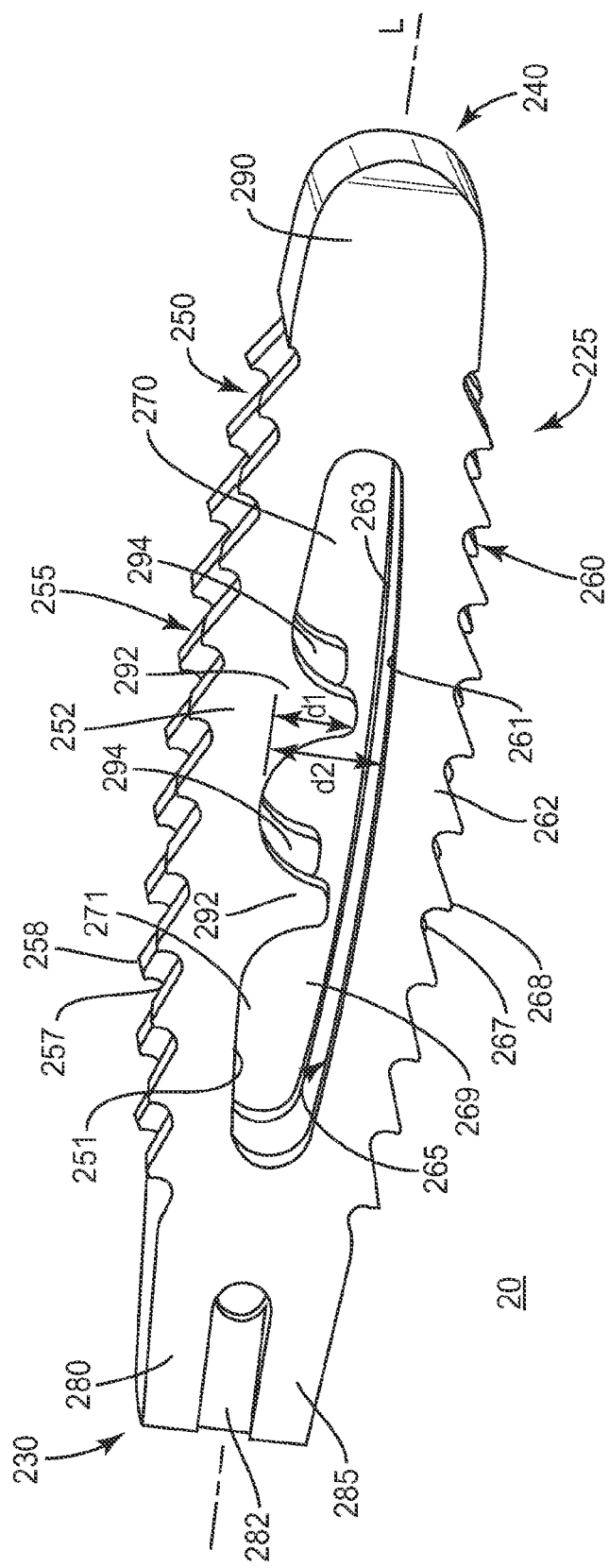
FIG. 5 is a perspective view of one embodiment of the implant shown in FIG. 1.

In one embodiment, as shown in FIG. 5, the interbody implant system includes an intervertebral fusion implant 20, similar to the configuration and methods described above, which includes a body 225 defining a longitudinal axis L and extending between an anterior end 230 and a posterior end 240. Body 225 includes a first wall 250 and a second wall 260. First wall 250 is configured to engage a first vertebral surface and second wall 260 is configured to engage a second vertebral surface facing in an orientation opposing the first vertebral surface. Walls 250, 260 extend in a substantially linear orientation along axis L from anterior end 230.

Walls 250, 260 are flexible and relatively movable. Wall 250 includes an outer wall surface 257 configured to engage a first vertebral endplate surface. Wall surface 257 includes a plurality of raised elements 258. Wall 260 includes an outer wall surface 267 configured to engage a first vertebral endplate surface. Wall surface 267 includes a plurality of raised elements 268.

First wall 250 includes an inner surface 251 extending from anterior end 230. Inner surface 251 has a substantially smooth and/or even surface and is arcuately shaped in a concave configuration. Second wall 260 includes an inner surface 261 extending from anterior end 230. Inner surface 261 has a substantially smooth and/or even surface and is arcuately shaped in a concave configuration.

First wall 250 and second wall 260 are configured to form a cavity 270. First wall 250 includes a pair of lateral spaced apart arms 252, 253 extending along axis L between anterior end 230 and posterior end 240. Lateral arms 252, 253 are spaced apart to define an opening 255. Opening 255 is in communication with cavity 270.

Second wall 260 includes a pair of lateral spaced apart arms 262, 263 extending along axis L between anterior end 230 and posterior end 240. Lateral arms 262, 263 are spaced apart to define an opening 265. Opening 265 is in communication with cavity 270. Arms 252, 262 define a lateral opening 269 and arms 253, 263 define a lateral opening 271. Openings 269, 271 communicate with cavity 270. It is envisioned that cavity 270, opening 255, opening 265, opening 269 and/or opening 271 may be configured for packing of at least one agent, for example, bone graft.

Arm 252 includes spaced apart posts 292 disposed in series along axis L. Each of posts 292 extend a first distance d1 from inner surface 251. Arm 253 includes spaced apart posts 294 disposed in series along axis L. Each of posts 294 extend a first distance d1 from inner surface 251. Posts 292 are laterally spaced apart from posts 294. It is envisioned that arms 252, 253, 262, 263 may include one or a plurality of posts. It is further envisioned that the posts may be flexible, semi-rigid or rigid. It is contemplated that the posts may be disposed in various orientations relative to axis L, such as, for example, coaxial, parallel, perpendicular, angular, offset and/or staggered. It is further contemplated that the posts may be monolithically formed, integrally connected and/or fastened with attaching elements to the arms.

Arms 252, 253, 262, 263 are connected to a solid nose portion 291 of posterior end 240. Nose portion 291 has tapered thickness. Arms 252, 253, 262, 263 are connected to arms 280, 285 that extend outwardly from anterior end 230. Arms 280, 285 form a cavity 282. Arms 280, 285 are configured to collapse into cavity 282 during deformation, as described below.

In operation, walls 250, 260 are configured to collapse in cavity 270 such that body 225 selectively deforms in a range between the difference of distance d1 and distance d2 between walls 250, 260 such that body 225 is deformed relative to the first configuration to adapt to an orientation of the first vertebral surface and the second vertebral surface. Distance d2 is greater than distance d1. Wall 250 is movable relative to wall 260 such that body 225 is selectively deformable, similar to that described herein, from a first, initial implanted configuration such that walls 250, 260 are spaced apart distance d2 and body 225 is disposed between a first vertebral surface and a second vertebral surface for fixation thereof, and a second configuration such that body 225 is selectively deformed according to a difference between distance d2 and distance d1 to adapt to an orientation of the vertebral surfaces.

Figure 6:
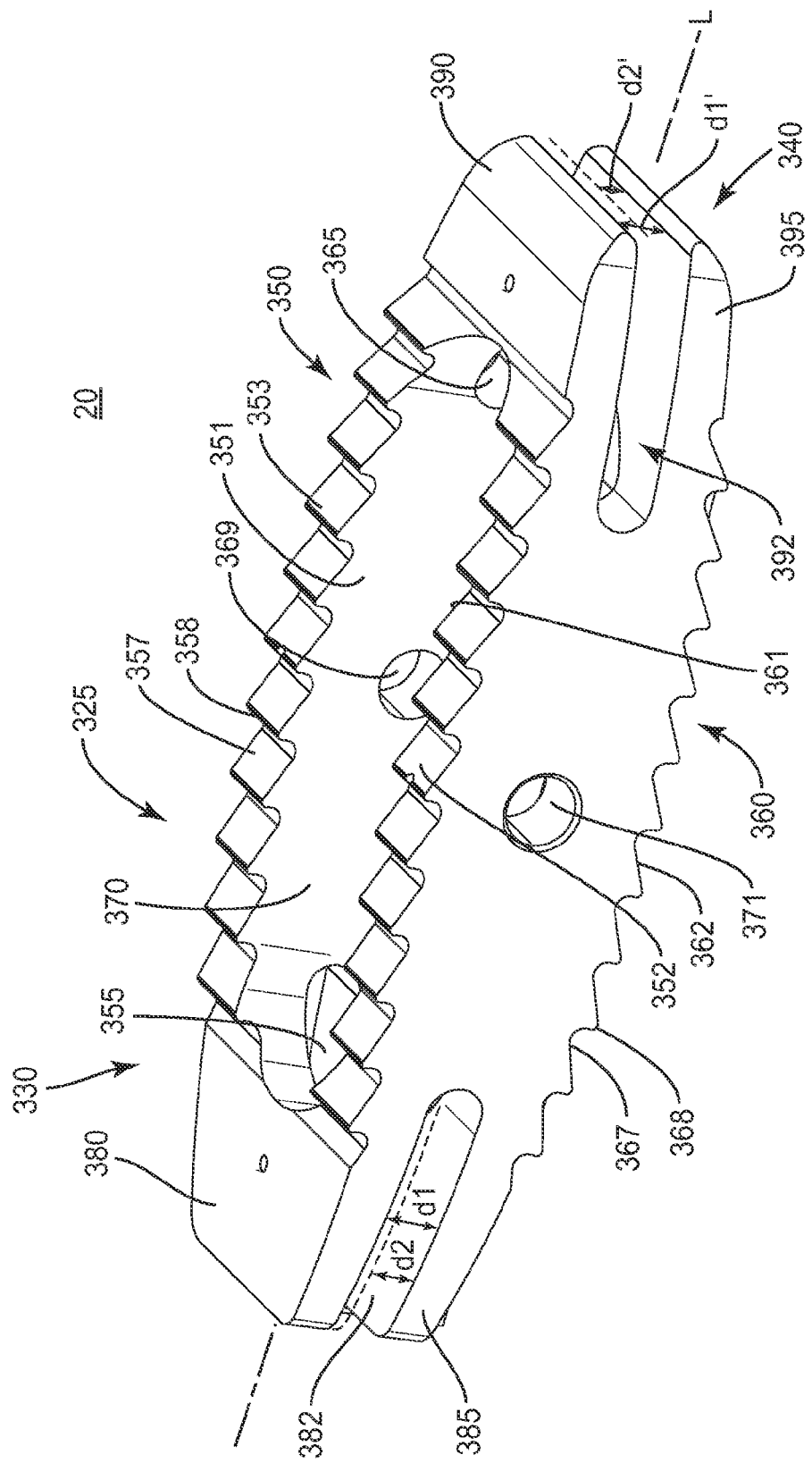
FIG. 6 is a perspective view of one embodiment of the implant shown in FIG. 1.

In one embodiment, as shown in FIG. 6, the interbody implant system includes an intervertebral fusion implant 20, similar to the configuration and methods described above, which includes a body 325 defining a longitudinal axis L and extending between an anterior end 330 and a posterior end 340. Body 325 includes a first wall 350 and a second wall 360. First wall 350 is configured to engage a first vertebral surface and second wall 360 is configured to engage a second vertebral surface facing in an orientation opposing the first vertebral surface. Walls 350, 360 extend in a substantially linear orientation along axis L.

Walls 350, 360 are flexible and relatively movable. Wall 350 includes an outer wall surface 357 configured to engage a first vertebral endplate surface. Wall surface 357 includes a plurality of raised elements 358. Wall 360 includes an outer wall surface 367 configured to engage a first vertebral endplate surface. Wall surface 367 includes a plurality of raised elements 368.

Body 325 includes a first lateral wall having an inner surface 351 extending between anterior end 330 and posterior end 340. Inner surface 351 has a substantially smooth and/or even surface and is arcuately shaped in a concave configuration. Body 325 includes a second lateral wall having an inner surface 361 extending between anterior end 330 and posterior end 340. Inner surface 361 has a substantially smooth and/or even surface and is arcuately shaped in a concave configuration.

Inner surfaces 351, 361 are configured to form a cavity 370, which includes openings in surfaces 357, 367. Inner surfaces 351, 361 are connected to define an opening 355 disposed adjacent anterior end 330 and an opening 365 disposed adjacent posterior end 340. Openings 355, 365 are in communication with cavity 370. The first lateral wall including inner surface 351 defines a lateral opening 369 and the second lateral wall including inner surface 361 defines a lateral opening 371. Openings 369, 371 communicate with cavity 370. It is envisioned that cavity 370, opening 355, opening 365, opening 369 and/or opening 371 may be configured for packing of at least one agent, for example, bone graft.

Walls 350, 360 are connected to arms 380, 385 that extend outwardly from anterior end 330. Arms 380, 385 form a cavity 382. Arms 380, 385 are configured to collapse into cavity 382 during deformation, as described below. Walls 350, 360 are connected to arms 390, 395 that extend outwardly from posterior end 340. Arms 390, 395 form a cavity 392. Arms 390, 395 are configured to collapse into cavity 392 during deformation, as described below.

In operation, arms 380, 385 are configured to collapse in cavity 382 such that body 325 selectively deforms in a range between a spaced apart distance d1 between arms 380, 385 and a relative distance d2 between arms 380, 385. Arms 390, 395 are configured to collapse in cavity 392 such that body 325 selectively deforms in a range between a spaced apart distance d1' between arms 390, 395 and a relative distance d2' between arms 390, 395. Arms 380, 385, 390, 395 collapse such that intervertebral fusion implant 20 is disposable between a first, initial implanted configuration and a second configuration, similar to that described herein, such that body 325 is deformed relative to the first configuration to adapt to an orientation of the first vertebral surface and the second vertebral surface. It is envisioned that distance d2 can include a range of distance including distance d1, a distance less than distance d1 and distance substantially equal to zero such that arms 380, 385 are disposed in a flush engagement. It is envisioned that distance d2' can include a range of distance including distance d1', a distance less than distance d1' and distance substantially equal to zero such that arms 390, 395 are disposed in a flush engagement.

Figure 7:
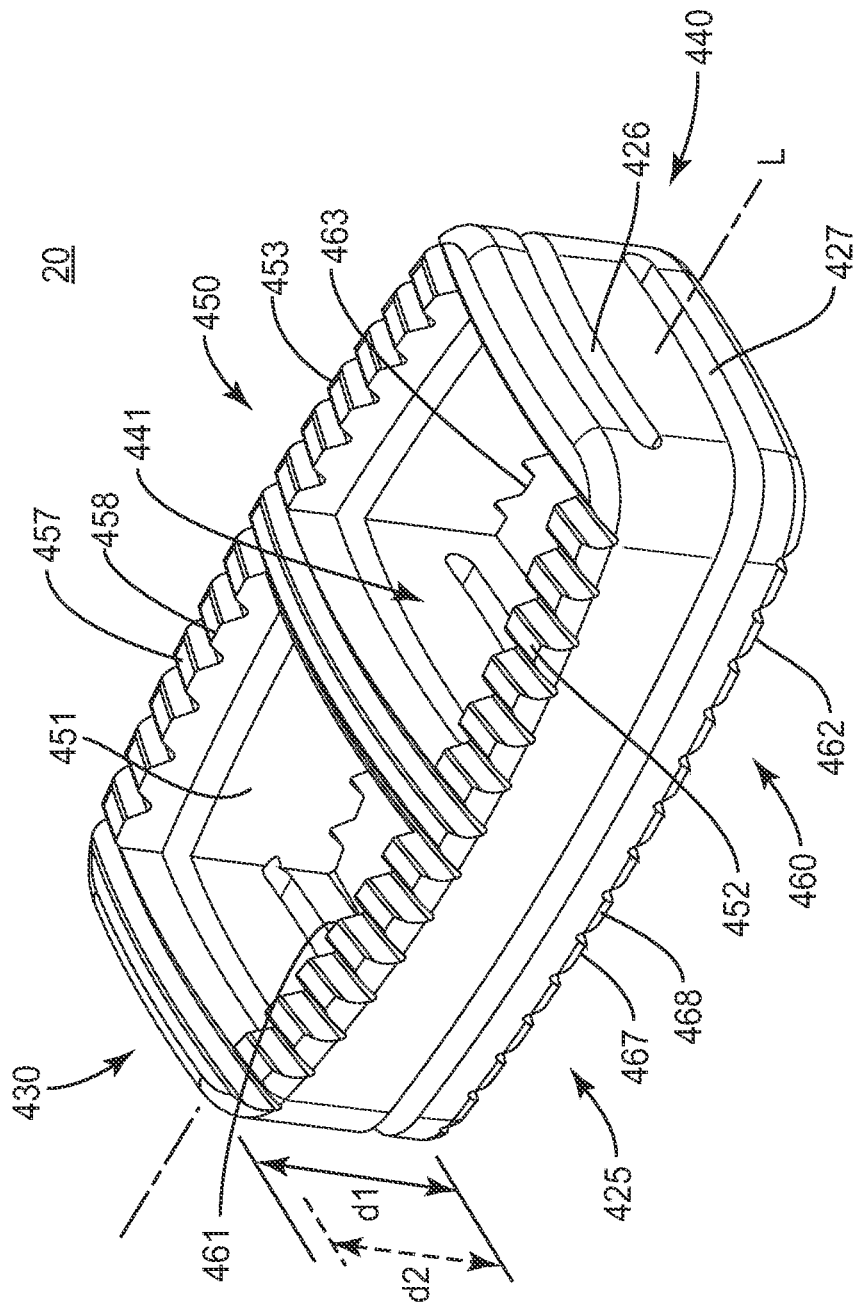
FIG. 7 is a perspective view of one embodiment of the implant shown in FIG. 1.

In one embodiment, as shown in FIG. 7, the interbody implant system includes an intervertebral fusion implant 20, similar to the configuration and methods described above, which includes a body 425 defining a longitudinal axis L and extending between an anterior end 430 and a posterior end 440. Body 425 includes a first wall 450 and a second wall 460. First wall 450 is configured to engage a first vertebral surface and second wall 460 is configured to engage a second vertebral surface facing in an orientation opposing the first vertebral surface. Walls 450, 460 extend in a substantially linear orientation along axis L from anterior end 430.

Walls 450, 460 are flexible and relatively movable. Wall 450 includes an outer wall surface 457 configured to engage a first vertebral endplate surface. Wall surface 457 includes a plurality of raised elements 458. Wall 460 includes an outer wall surface 467 configured to engage a first vertebral endplate surface. Wall surface 467 includes a plurality of raised elements 468.

Body 425 includes a first lateral wall that includes an inner surface 451 extending between anterior end 430 and posterior end 440. Inner surface 451 has a substantially smooth and/or even surface and is arcuately shaped in a concave configuration. Body 425 includes a second lateral wall that includes an inner surface 461 extending between anterior end 430 and posterior end 440. Inner surface 461 has a substantially smooth and/or even surface and is arcuately shaped in a concave configuration. Body 425 includes an intermediate member 441 extending between inner surface 451 and inner surface 461. Body 425 has an S-shaped cross section that defines an upper cavity 426 and a lower cavity 427. Cavities 426, 427 facilitate deformation transverse to axis L, as will be described.

Inner surface 451 and inner surface 461 are configured to form a cavity 470. Intermediate member 441 separates cavity 470 into section 470a and 470b. Sections 470a, 470b communicate via cavities 426, 427. It is envisioned that cavity 470, section 470a, section 470b and/or cavities 426, 427 may be configured for packing of at least one agent, for example, bone graft.

In operation, walls 450, 460 are configured to collapse in cavities 426, 427 such that body 425 selectively deforms in a range between a spaced apart distance d1 of walls 450, 460 and a relative distance d2 of walls 450, 160 such that intervertebral fusion implant 20 is disposable between a first, initial implanted configuration and a second configuration, similar to that described herein, such that body 425 is deformed relative to the first configuration to adapt to an orientation of the first vertebral surface and the second vertebral surface. Body 425 is also deformable transverse to axis L due to the configuration of cavities 426, 427.

Figure 8:
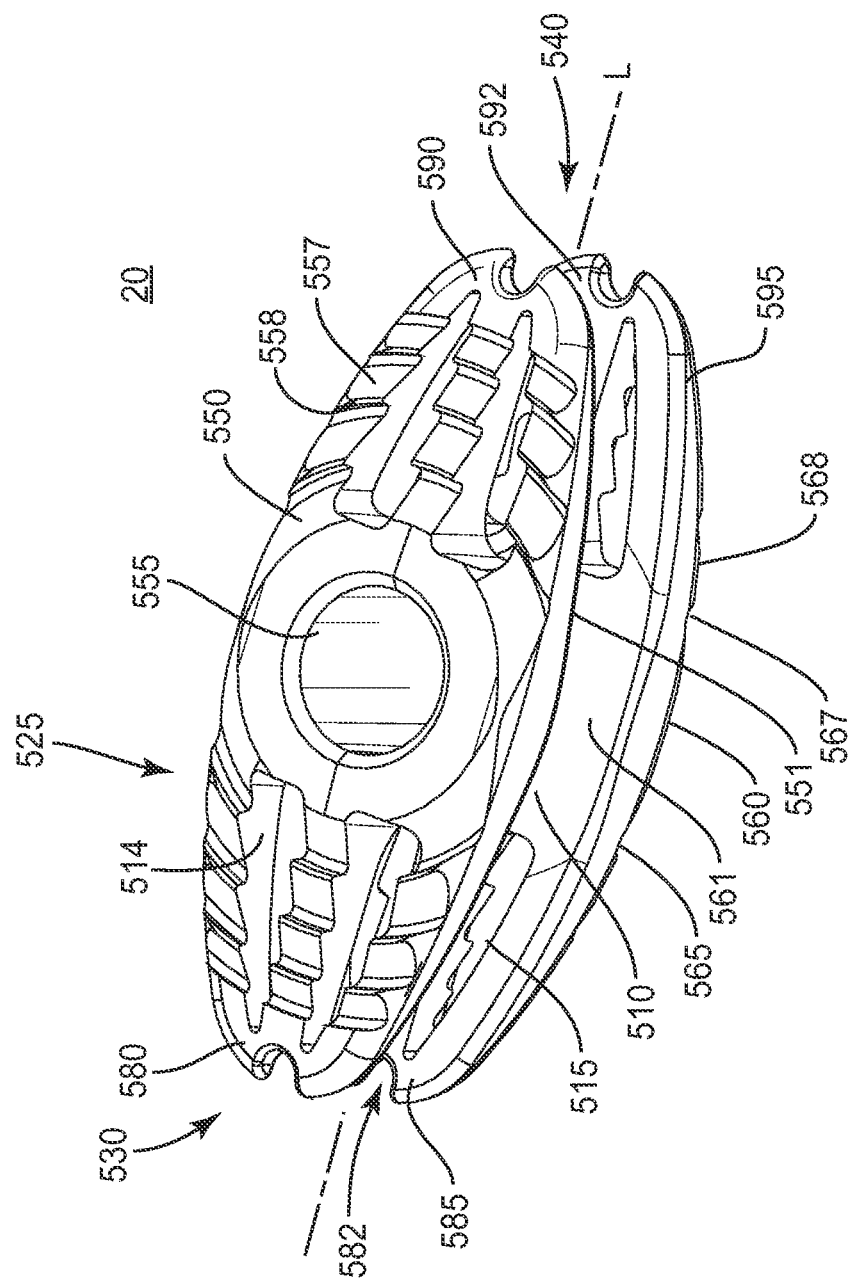
FIG. 8 is a perspective view of one embodiment of the implant shown in FIG. 1.
Figure 9:
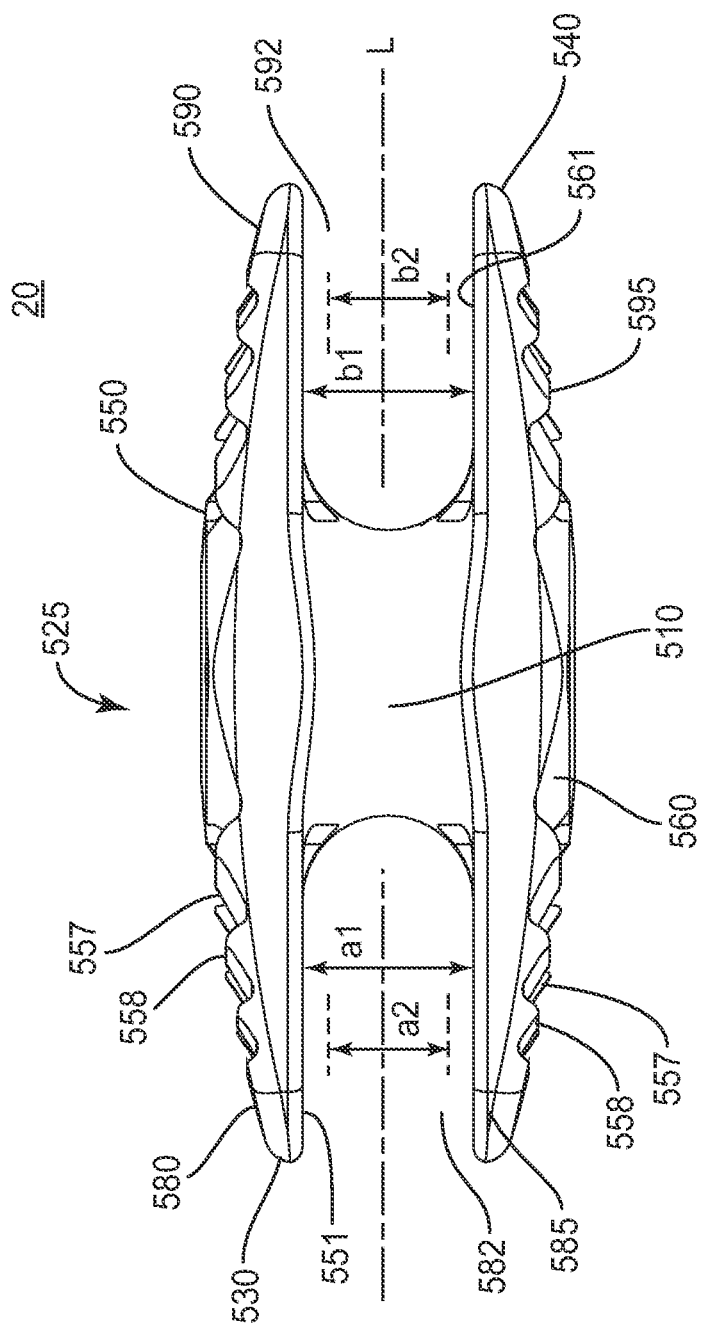
FIG. 9 is a side perspective view of one embodiment of the implant shown in FIG. 8.

In one embodiment, as shown in FIGS. 8 and 9, the interbody implant system includes an intervertebral fusion implant 20, similar to the configuration and methods described above, which includes a body 525 defining a longitudinal axis L and extending between an anterior end 530 and a posterior end 540. Body 525 includes a first wall 550 and a second wall 560. First wall 550 is configured to engage a first vertebral surface and second wall 560 is configured to engage a second vertebral surface facing in an orientation opposing the first vertebral surface. Walls 550, 560 extend in a substantially linear orientation along axis L.

Walls 550, 560 are flexible and relatively movable. Wall 550 includes an outer wall surface 557 configured to engage a first vertebral endplate surface. Wall surface 557 includes a plurality of raised elements 558. Wall 560 includes an outer wall surface 567 configured to engage a first vertebral endplate surface. Wall surface 567 includes a plurality of raised elements 568.

Body 525 includes an intermediate member 510 disposed between anterior end 530 and posterior end 540. Intermediate member 510 connects wall 550 with wall 560. Wall 550 includes an inner surface 551 extending between anterior end 530 and posterior end 540. Inner surface 551 has a substantially smooth and/or even surface and is substantially planar. Wall 560 includes an inner surface 561 extending between anterior end 530 and posterior end 540. Inner surface 561 has a substantially smooth and/or even surface and is substantially planar. Wall 550 includes an opening 555 and wall 560 includes an opening 565. Openings 555, 565 communicate via a passageway of intermediate member 510. Wall 550 includes a plurality of angular openings 514 and wall 560 includes a plurality of angular openings 515.

Inner surfaces 551, 561 and intermediate member 510 are configured to form a cavity 570. Openings 514, 515, 555, 565 are in communication with cavity 570. It is envisioned that cavity 570, opening 514, opening 515, opening 555 and/or opening 565 may be configured for packing of at least one agent, for example, bone graft.

Walls 550, 560 include arms 580, 585 that extend outwardly from intermediate member 510. Arms 580, 585 form a cavity 582. Arms 580, 585 are configured to collapse into cavity 582 during deformation, as described below. Walls 550, 560 include arms 590, 595 that extend outwardly from intermediate member 510. Arms 590, 595 form a cavity 592. Arms 590, 595 are configured to collapse into cavity 592 during deformation, as described below.

In operation, arms 580, 585 are configured to collapse in cavity 582 such that body 525 selectively deforms in a range between a spaced apart distance a1 between arms 580, 585 and a relative distance a2 between arms 580, 385. Arms 590, 595 are configured to collapse in cavity 592 such that body 525 selectively deforms in a range between a spaced apart distance b1 between arms 590, 595 and a relative distance b2 between arms 590, 595. Arms 580, 585, 590, 595 collapse such that intervertebral fusion implant 20 is disposable between a first, initial implanted configuration and a second configuration, similar to that described herein, such that body 525 is deformed relative to the first configuration to adapt to an orientation of the first vertebral surface and the second vertebral surface. It is envisioned that distance a2 can include a range of distance including distance a1, a distance less than distance a1 and distance substantially equal to zero such that arms 580, 585 are disposed in a flush engagement. It is envisioned that distance b2 can include a range of distance including distance b1, a distance less than distance b1 and distance substantially equal to zero such that arms 590, 595 are disposed in a flush engagement.

Figure 10:
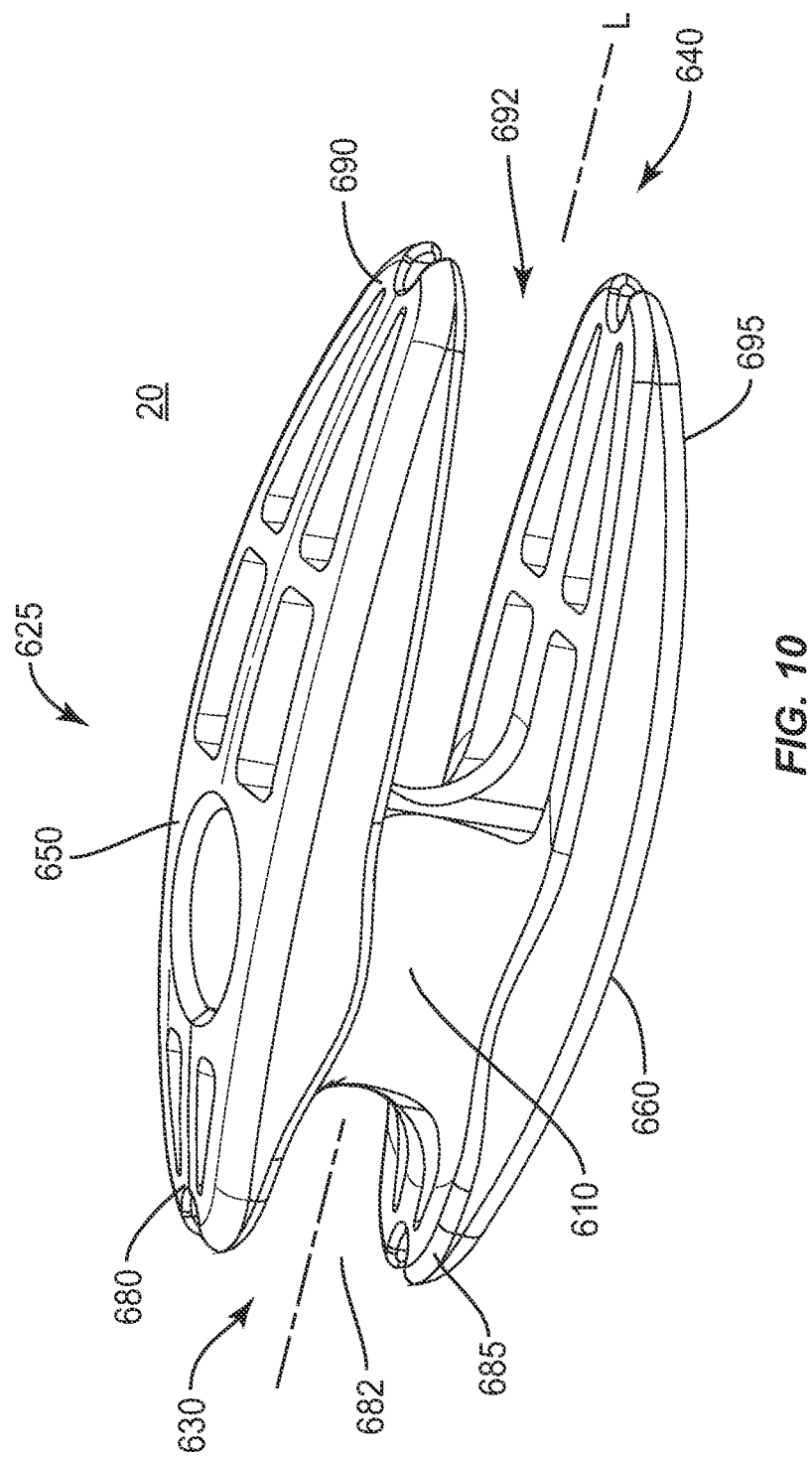
FIG. 10 is a perspective view of one embodiment of the implant shown in FIG. 1.

In one embodiment, as shown in FIG. 10, the interbody implant system includes an intervertebral fusion implant 20, similar to the configuration and methods described with regard to FIGS. 8 and 9, which includes a body 625 defining a longitudinal axis L and extending between an anterior end 630 and a posterior end 640. Body 625 includes a first wall 650 and a second wall 660.

Walls 650, 660 are flexible and relatively movable. Body 625 includes an intermediate member 610 disposed between anterior end 630 and posterior end 640, and offset from a central portion of body 625. Intermediate member 610 connects wall 650 with wall 660.

Walls 650, 660 include arms 680, 685 that extend outwardly from intermediate member 610. Arms 680, 685 form a cavity 682. Arms 680, 685 are configured to collapse into cavity 682 during deformation. Walls 650, 660 include arms 690, 695 that extend outwardly from intermediate member 610. Arms 690, 695 form a cavity 692. Arms 690, 695 are configured to collapse into cavity 692 during deformation. Arms 690, 695 extend a greater length relative to arms 680, 685. This configuration provides greater flexibility to implant 20 adjacent posterior end 640 and facilitates restoration of lordosis by providing a settled angular configuration of implant 20. It is contemplated that implant 20 maintains a height of post 610 while allowing for deformation of the walls 650, 660 along the longitudinal axis.

Figure 11:
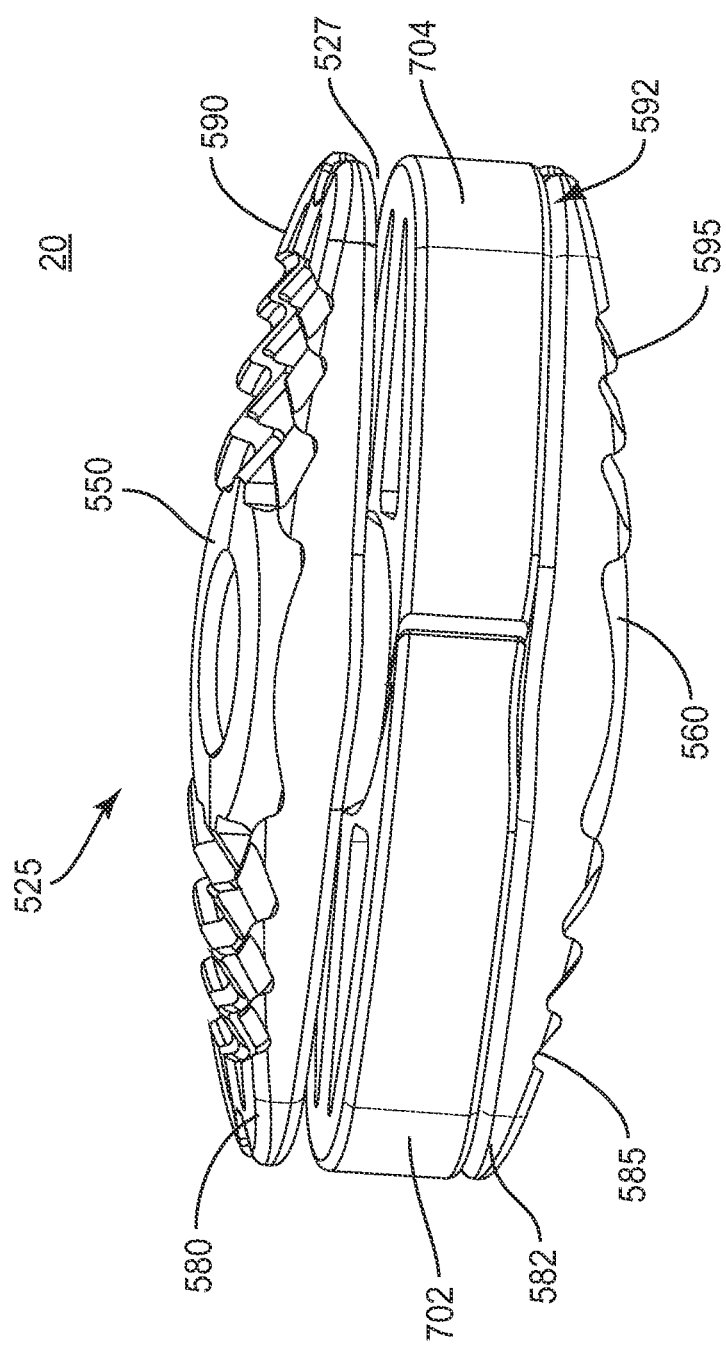
FIG. 11 is a perspective view of one embodiment of the implant shown in FIG. 1.

In one embodiment, as shown in FIG. 11, the interbody implant system includes an intervertebral fusion implant 20, described with regard to FIGS. 8 and 9, which includes a first rigid member 702 disposed in cavity 582 and a second rigid member 704 disposed in cavity 592. Rigid members 702, 704 prevent collapse and/or allow only slight collapse of walls 550, 560. It is contemplated that members 702, 704 may be monolithically formed, integrally connected or attached. It is further contemplated that members 702, 704 may be semi-rigid or flexible.

Figure 12:
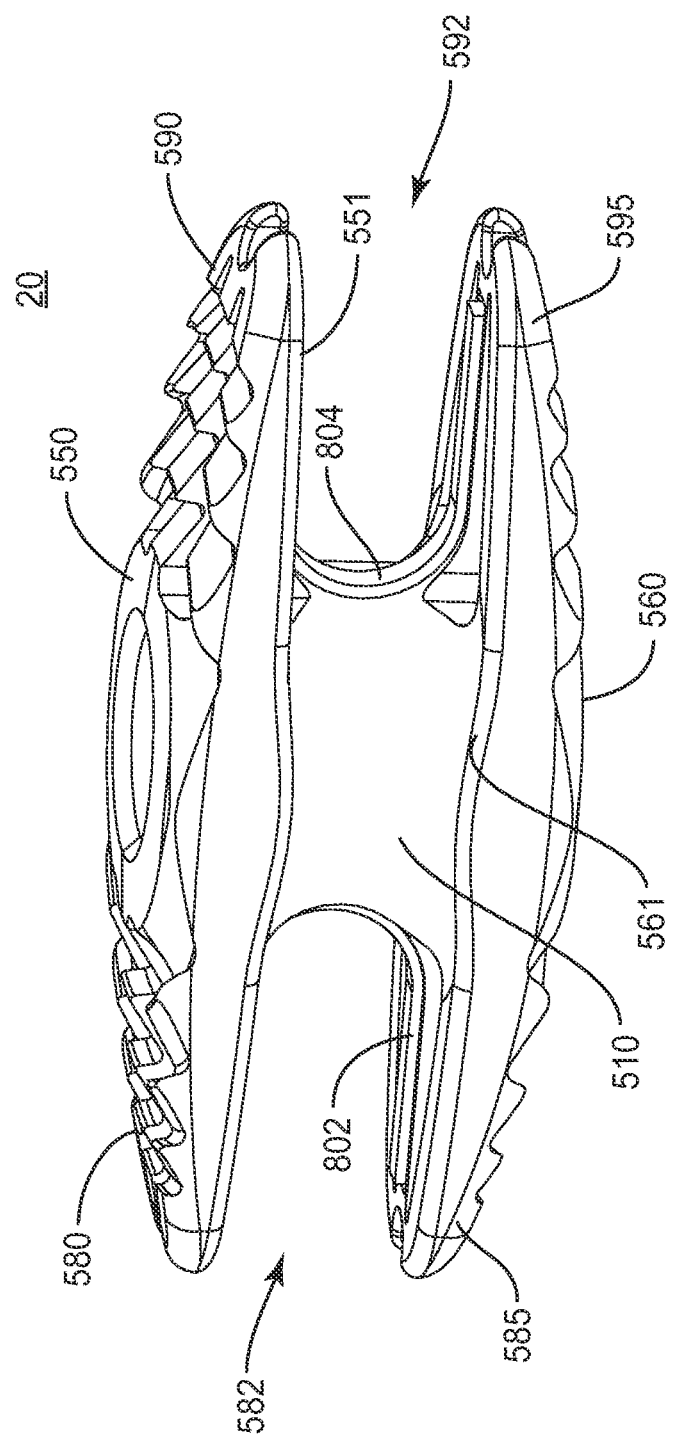
FIG. 12 is a perspective view of one embodiment of the implant shown in FIG. 1.

In one embodiment, as shown in FIG. 12, the interbody implant system includes an intervertebral fusion implant 20, described with regard to FIGS. 8 and 9, which includes a first arcuate rigid member 802 disposed in cavity 582 and a second arcuate rigid member 804 disposed in cavity 592. Rigid members 802, 804 prevent collapse and/or allow only slight collapse of walls 550, 560. It is contemplated that members 802, 804 are disposed in a continuous cavity formed in inner surfaces 551, 561 and intermediate member 510. It is further contemplated that members 802, 804 may be semi-rigid or flexible.

Figure 13:
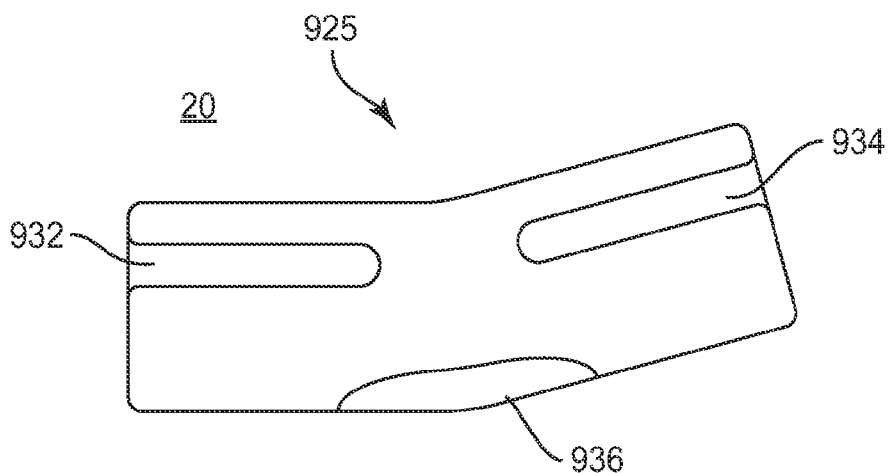
FIG. 13 is a side view of one embodiment of the implant shown in FIG. 1.
Figure 14:
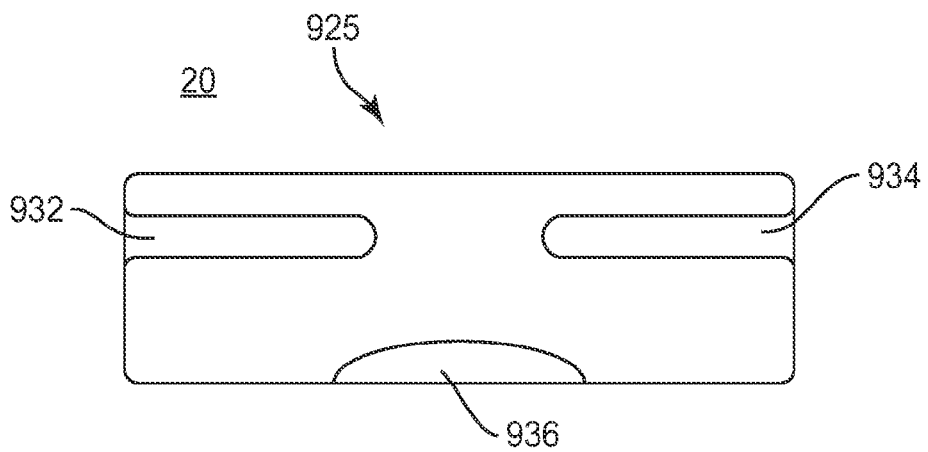
FIG. 14 is a perspective view of one embodiment of the implant shown in FIG. 1.
Figure 15:
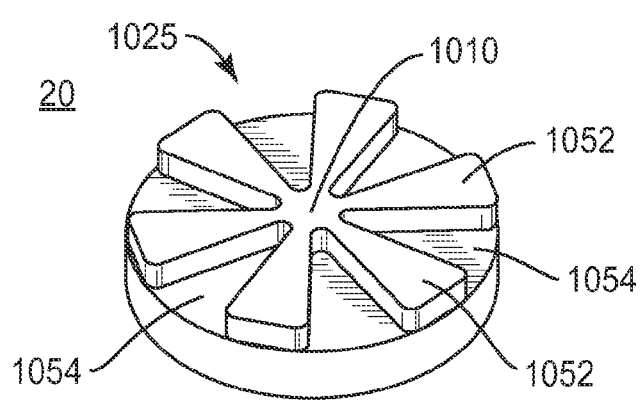
FIG. 15 is a side view of one embodiment of the implant shown in FIG. 1.

In one embodiment, as shown in FIGS. 13 and 14, the interbody implant system includes an intervertebral fusion implant 20. Implant 20 includes a body 925 having an anterior cavity 932, a posterior cavity 934 and an intermediate cavity 936. Posterior cavity 934 is angularly offset from anterior cavity 932 in the initial configuration, as shown in FIG. 13. This offset angled configuration facilitates insertion into the intervertebral body space and at angle. In the final configuration, anterior cavity 932, a posterior cavity 934 and an intermediate cavity 936 are disposed in a alignment along longitudinal access. In one embodiment, as shown in FIG. 15, the interbody implant system includes an intervertebral fusion implant 20, similar to the configuration and methods described above, which includes a disc shaped body 1025 having radial arms 1052 disposed circumferentially about an intermediate member 1010 and defining radial cavities 1054 disposed circumferentially. Radial arms 1052 and the and the implant body 1025 can deform to provide optimum configuration with the end plates.

Figure 16:
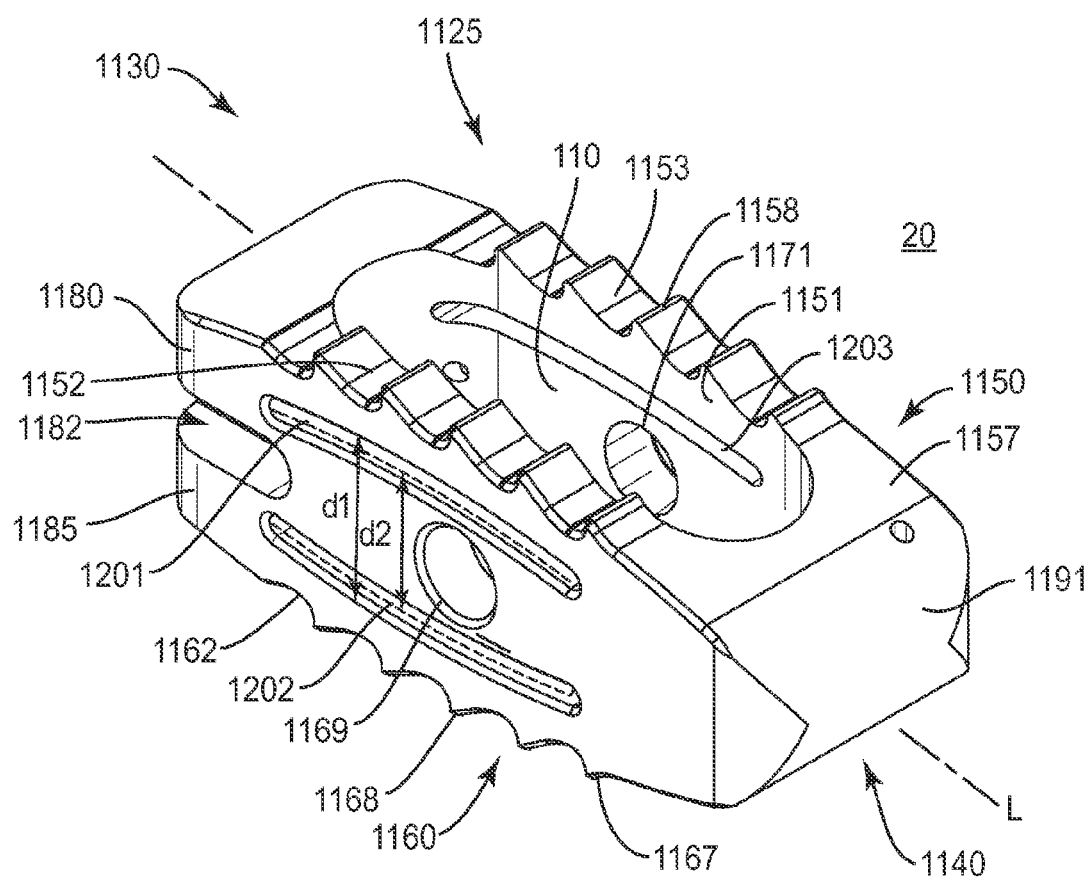
FIG. 16 is a perspective view of one embodiment of the implant shown in FIG. 1.

In one embodiment, as shown in FIG. 16, the interbody implant system includes an intervertebral fusion implant 20, similar to the configuration and methods described above with regard to FIGS. 1-4, which includes a body 1125 defining a longitudinal axis L and extending between an anterior end 1130 and a posterior end 1140. Body 1125 includes a first wall 1150 and a second wall 1160. First wall 1150 is configured to engage a first vertebral surface and second wall 1160 is configured to engage a second vertebral surface facing in an orientation opposing the first vertebral surface. Walls 1150, 1160 extend in a substantially linear orientation along axis L from anterior end 1130.

Walls 1150, 1160 are flexible and relatively movable. Wall 1150 includes an outer wall surface 1157 configured to engage a first vertebral endplate surface. Wall surface 1157 includes a plurality of raised elements 1158. Wall 1160 includes an outer wall surface 1167 configured to engage a first vertebral endplate surface. Wall surface 1167 includes a plurality of raised elements 1168.

First wall 1150 includes an inner surface 1151 extending from anterior end 1130. Inner surface 1151 has a substantially smooth and/or even surface and is arcuately shaped in a concave configuration. Second wall 1160 includes an inner surface 1161 extending from anterior end 1130. Inner surface 1161 has a substantially smooth and/or even surface and is arcuately shaped in a concave configuration.

First wall 1150 and second wall 1160 are configured to form a cavity 1170. First wall 1150 includes a pair of lateral spaced apart arms 1152, 1153 extending along axis L between anterior end 1130 and posterior end 1140. Lateral arms 1152, 1153 are spaced apart to define an opening 1155. Opening 1155 is in communication with cavity 1170.

Second wall 1160 includes a pair of lateral spaced apart arms 1162, 1163 extending along axis L between anterior end 1130 and posterior end 1140. Lateral arms 1152, 1153, 1162, 1163 include openings 1201, 1203, 1202, 1204 (not shown). Openings 1201, 1203, 1202, 1204 are in communication with cavity 1170. Arms 1152, 1162 also define a circular opening 1169 and arms 1153, 1163 define a circular opening 1171. Openings 1169, 1171 which are in communication with cavity 1170. It is envisioned that cavity 1170, openings 1201, 1203, 1202, 1204, opening 1169 and/or opening 1171 may be configured for packing of at least one agent, for example, bone graft.

Arms 1152, 1153, 1162, 1163 are connected to a solid nose portion 1191 of posterior end 1140. Nose portion 1191 has tapered thickness. Arms 1152, 1153, 1162, 1163 are connected to arms 1180, 1185 that extend outwardly from anterior end 1130. Arms 1180, 1185 form a cavity 1182. Arms 1180, 1185 are configured to collapse into cavity 1182 during deformation, as described below.

In operation, walls 1150, 1610 are configured to collapse showing a deformation in openings 1169 and 1171 and openings 1201, 1202, 1203, 1204 such that body 1125 selectively deforms in a range between a spaced apart distance d1 between walls 1150, 1160 and a relative distance d2 between walls 1150, 1160 such that intervertebral fusion implant 20 is disposable between a first, initial implanted configuration and a second configuration, similar to that described herein, such that body 1125 is deformed relative to the first configuration to adapt to an orientation of the first vertebral surface and the second vertebral surface. It is envisioned that distance d2 can include a range of distance including distance d1, a distance less than distance d1 and distance substantially equal to zero such that walls 1150, 1160 are disposed in a flush engagement.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An intervertebral fusion implant comprising:
a body defining a longitudinal axis and extending between a first end having an end wall and a second end, the body defining a first wall configured for engaging a first vertebral surface and a second wall configured for engaging a second vertebral surface, the first and second walls each extending in a cantilevered configuration from the end wall, the end wall having an uninterrupted configuration, the first wall including a first pair of lateral arms and the second wall including a second pair of lateral arms, the first pair of lateral arms being connected to one another at the second end by a transverse portion of the first wall, each of the pair of lateral arms extending between the first end and the second end, and defining a cavity therebetween, the arms being configured to collapse in the cavity during deformation,
wherein the first wall is movable relative to the second wall such that the body is deformable from a first, initial implanted configuration such that the body is disposed between the first vertebral surface and the second vertebral surface for fixation thereof and a second configuration such that the body is deformed relative to the first configuration to adapt to an orientation of the first vertebral surface and the second vertebral surface.

2. An intervertebral fusion implant as recited in claim 1 wherein the first and second walls are configured to collapse in the cavity during a selective amount of deformation, the selective amount of deformation including a range between a first spaced apart distance between the first and second walls and engagement of the first and second walls.

3. An intervertebral fixation implant as recited in claim 1 wherein the first and second walls extend in an arcuate configuration from the end wall.

4. An intervertebral fixation implant as recited in claim 1 wherein the cavity includes a bone graft receptacle.

5. An intervertebral fusion implant as recited in claim 1 wherein the first wall includes recesses disposed in lateral portions of the body, each of the recesses defining an opening configured to provide a relief to facilitate relative movement of the first wall and the second wall.

6. An intervertebral fusion implant as recited in claim 5 wherein the openings are substantially circular.

7. An intervertebral fusion implant as recited in claim 5 wherein the recesses include a pair of spaced apart recesses.

8. An intervertebral fusion implant as recited in claim 1 wherein the first and second walls are disposed in flush engagement when the body is in the second configuration.

9. An intervertebral fusion implant as recited in claim 1 wherein the first and second walls are spaced apart from one another at the second end of the body when the body is in the second configuration.

10. An intervertebral fixation implant as recited in claim 1 wherein the first pair of lateral arms are spaced apart from one another to define an opening therebetween that is in communication with the cavity.

11. An intervertebral fixation implant as recited in claim 10 wherein the second pair of lateral arms are spaced apart from one another to define an opening therebetween that is in communication with the cavity, the second pair of lateral arms being connected to one another at the second end by a transverse portion of the second wall.

12. An intervertebral fixation implant as recited in claim 11 wherein at least one of the openings has a bone graft disposed therein.

13. An intervertebral fixation implant as recited in claim 1 wherein the first end comprises a concave inner surface that extends between the first pair of lateral arms and between the second pair of lateral arms, the inner surface defining a portion of the cavity.

14. An intervertebral fixation implant as recited in claim 1 wherein the first and second walls are flexible.

15. An intervertebral fixation implant as recited in claim 1 wherein the first and second walls each have a substantially rectangular cross sectional configuration.

16. An intervertebral fixation implant as recited in claim 1 wherein at least one of the first and second walls comprises an outer wall surface including a plurality of raised elements configured to enhance engagement with one of the vertebral surfaces.

17. An intervertebral fixation implant as recited in claim 16 wherein the raised elements are fabricated from a different material than the body.

18. An intervertebral fixation implant as recited in claim 16 wherein the outer wall surface of the first wall comprises a first section adjacent the first end, a second section adjacent the second end and an intermediate section between the first and second sections, the first and second sections each being free of the raised elements and the intermediate section including the raised elements.

19. An intervertebral fixation implant as recited in claim 1 wherein the first wall includes an inner surface extending from the first end that is smooth and arcuately shaped in a concave configuration and the second wall includes an inner surface extending from the first end that is smooth and arcuately shaped in a convex configuration.

20. An intervertebral fixation implant comprising:
a body defining a longitudinal axis and extending between a first end having a first end wall and a second end, the body defining a first wall configured for engaging a first vertebral surface and a second wall configured for engaging a second vertebral surface, the first and second walls each extending from the end wall in a cantilevered configuration, the end wall having an uninterrupted configuration, the first wall including a first pair of lateral arms and the second wall including a second pair of lateral arms, the first pair of lateral arms being connected to one another at the second end by a transverse portion of the first wall, each of the pair of lateral arms extending between the first end and the second end, and defining a cavity therebetween, the first wall defining an arcuate inner surface and the second wall defining an arcuate inner surface, the walls being configured to collapse in the cavity such that the body selectively deforms in a range between a spaced apart distance between the first and second walls and engagement of the first and second walls, wherein the first wall is movable relative to the second wall such that the body is deformable from a first, initial implanted configuration such that the body is disposed between the first vertebral surface and the second vertebral surface for fixation thereof, and a second configuration such that the body is deformed relative to the first configuration to adapt to surface geometry and height of an intervertebral space between the first vertebral surface and the second vertebral surface.

\* \* \* \* \*

UNITED STATES PATENT AND TRADEMARK OFFICE
CERTIFICATE OF CORRECTION

PATENT NO. : 9,149,366 B2
APPLICATION NO. : 13/826825
DATED : October 6, 2015
INVENTOR(S) : Prevost et al.

It is certified that error appears in the above-identified patent and that said Letters Patent is hereby corrected as shown below:

On the Title Page, in Item (73), under "Assignee", in Column 1, Line 1, delete "Warsaw (IN)" and insert -- Warsaw, IN (US) --, therefor.

In the Specification:

In Column 6, Line 18, delete "surface 58" and insert -- surface 57 --, therefor.

In Column 10, Line 11, delete "morphogenic" and insert -- morphogenetic --, therefor.

In Column 15, Line 10, delete "arms 580, 385." and insert -- arms 580, 585. --, therefor.

In the Claims:

In Column 17, Line 63, in Claim 3, delete "fixation" and insert -- fusion --, therefor.

In Column 17, Line 66, in Claim 4, delete "fixation" and insert -- fusion --, therefor.

In Column 18, Line 17, in Claim 10, delete "fixation" and insert -- fusion --, therefor.

In Column 18, Line 21, in Claim 11, delete "fixation" and insert -- fusion --, therefor.

In Column 18, Line 27, in Claim 12, delete "fixation" and insert -- fusion --, therefor.

In Column 18, Line 30, in Claim 13, delete "fixation" and insert -- fusion --, therefor.

In Column 18, Line 35, in Claim 14, delete "fixation" and insert -- fusion --, therefor.

In Column 18, Line 37, in Claim 15, delete "fixation" and insert -- fusion --, therefor.

Signed and Sealed this
Twenty-ninth Day of March, 2016

Michelle K. Lee
*Director of the United States Patent and Trademark Office*

CERTIFICATE OF CORRECTION (continued)
U.S. Pat. No. 9,149,366 B2

In the Claims:

In Column 18, Line 40, in Claim 16, delete "fixation" and insert -- fusion --, therefor.

In Column 18, Line 45, in Claim 17, delete "fixation" and insert -- fusion --, therefor.

In Column 18, Line 48, in Claim 18, delete "fixation" and insert -- fusion --, therefor.

In Column 18, Line 55, in Claim 19, delete "fixation" and insert -- fusion --, therefor.